United States Patent
Xu et al.

(10) Patent No.: US 11,572,359 B2
(45) Date of Patent: Feb. 7, 2023

(54) PARP/PI3K DOUBLE-TARGET INHIBIT CONTAINING PYRIDOPYRIMIDINE STRUCTURE

(71) Applicants: CHINA PHARMACEUTICAL UNIVERSITY, Nanjing (CN); HEFEI INDUSTRIAL PHARMACEUTICAL INSTITUTE CO., LTD., Hefei (CN)

(72) Inventors: Yungen Xu, Nanjing (CN); Qihua Zhu, Nanjing (CN); Junwei Wang, Nanjing (CN); Hui Li, Nanjing (CN); Zhaoxing Chu, Hefei (CN); Guangwei He, Hefei (CN)

(73) Assignee: CHINA PHARMACEUTICAL UNIVERSITY, Nanjing (CN)

( * ) Notice: Subject to any disclaimer, the term of this patent is extended or adjusted under 35 U.S.C. 154(b) by 280 days.

(21) Appl. No.: 16/769,893

(22) PCT Filed: Aug. 1, 2018

(86) PCT No.: PCT/CN2018/097980
§ 371 (c)(1),
(2) Date: Jun. 4, 2020

(87) PCT Pub. No.: WO2019/109647
PCT Pub. Date: Jun. 13, 2019

(65) Prior Publication Data
US 2021/0179610 A1    Jun. 17, 2021

(30) Foreign Application Priority Data

Dec. 5, 2017   (CN) .......................... 201711263824.8

(51) Int. Cl.
C07D 471/04    (2006.01)
A61P 35/00     (2006.01)
B01J 31/28     (2006.01)

(52) U.S. Cl.
CPC ............ *C07D 471/04* (2013.01); *A61P 35/00* (2018.01); *B01J 31/28* (2013.01)

(58) Field of Classification Search
CPC ........ C07D 471/04; A61P 35/00; B01J 31/28; B01J 31/2404; B01J 2231/4211; B01J 2531/824; A61K 31/5377
See application file for complete search history.

(56) References Cited

PUBLICATIONS

Wang, Y.-Q., "An update on poly (ADP-ribose) polymerase-1 (PARP-1) inhibitors: opportunities and challenges in cancer therapy." Journal of medicinal chemistry 59.21 (2016): 9575-9598.*

* cited by examiner

*Primary Examiner* — John M Mauro
(74) *Attorney, Agent, or Firm* — CMB Patent Consulting, LLC

(57) ABSTRACT

The present disclosure relates to the field of pharmaceutical chemistry, in particular to a class of PARP/PI3K double-target inhibitors (I) containing structures of 5,6,7,8-tetrahydropyrido[3,4-d]pyrimidine and phthalazin-1(2H)-one and a preparation method thereof. As proved by pharmacodynamic tests, the compounds of the present disclosure have PARP/PI3K double-target inhibitory activity and can be used for anti-tumor.

12 Claims, No Drawings

PARP/PI3K DOUBLE-TARGET INHIBIT CONTAINING PYRIDOPYRIMIDINE STRUCTURE

TECHNICAL FIELD

The present disclosure relates to the field of pharmaceutical chemistry, in particular to a class of PARP/PI3K double-target inhibitors containing structures of 5,6,7,8-tetrahydropyrido[3,4-d]pyrimidine and phthalazin-1(2H)-one, a preparation method thereof, a pharmaceutical composition containing the compounds and application thereof in the aspect of anti-tumor.

BACKGROUND ART

Poly(ADP-ribose) polymerase (PARP) is a multifunctional protein post-translational modification enzyme existing in most eukaryotic cells. At present, there are 18 subtypes that have been found in this family, of which PARP-1 accounts for the largest proportion. The PARP-1 involves treatment of diseases such as stroke, neurodegenerative diseases, myocardial ischemia, cancer, inflammations and diabetes, and plays a leading role in DNA damage repair. A PARP-1 inhibitor is a class of anti-tumor drugs that exert cytotoxicity by regulating DNA damage repair, and is one of the most exciting results in the field of tumor treatment research in the early 21st century. At present, three PARP inhibitors have been applied to clinical use, namely Olaparib launched in 2014, Rucaparib launched in 2016 and Niraparib launched in 2017, and the PARP inhibitors are mainly used for treatment of tumors such as breast cancer, ovarian cancer and peritoneal cancer. However, with the deepening of research and the successive release of clinical trial results, the limitations of the PARP-1 inhibitor are further presented. On the one hand, when the current PARP-1 inhibitor is used alone, it only has the curative effect against triple-negative breast cancer or ovarian cancer with BRCA1/2 deletion, which results in narrower indications of the PARP-1 inhibitor; and on the other hand, long-term use of the PARP-1 inhibitor also faces the problem of drug resistance, and these problems will adversely affect the clinical use of the PARP-1 inhibitor.

Phosphatidylinositol-3-kinase (PI3K) is an upstream molecule in a PI3K/Akt/mTOR signal transduction pathway. As a key nodal protein in the pathway, the PI3K can phosphorylate the 3-hydroxyl group of phosphatidylinositol 4,5-diphosphate (PIP2) to generate phosphatidylinositol 3,4,5-triphosphate (PIP3). As a second messenger, the PIP3 plays an important role in basic reactions such as survival, growth, proliferation and metabolism of cells. A tumor suppressor gene PTEN can dephosphorylate the PIP3 to generate the PIP2 and is an antagonist of PI3K catalysis. Abnormal activation of the PI3K can cause disorders of the pathway, causing a series of diseases including cancer, neurological disorders, autoimmune diseases, and hematopoietic diseases. The PI3K has become one of the important targets for tumor treatment research. There are mainly two PI3K inhibitors for clinical use, namely a PI3Kδ inhibitor Idelalisib launched in 2014 and a PI3Kα/PI3Kδ inhibition Copanlisib launched in 2017, which are mainly used for treating various lymphomas. In addition, there are still a plurality of PI3K inhibitors in the clinical research stage, but there are no reports of PARP-1/PI3K double-target inhibitors at present.

SUMMARY OF THE INVENTION

The present disclosure discloses a class of compounds of a formula (I). Pharmacodynamic test results show that the compounds or pharmaceutically acceptable salts thereof in the present disclosure can simultaneously act on two targets, i.e., PARP-1 and PI3K, and can be used as a single therapeutic agent for tumors, or used in combination with other anti-tumor drugs to achieve the purposes of improving the tumor curing effect and reducing dose and toxicity.

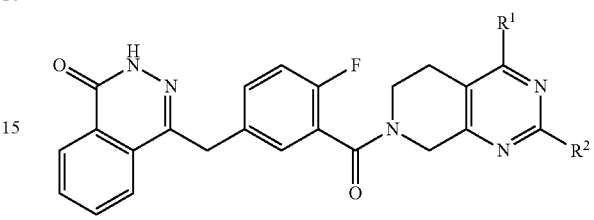

$R^1$ represents

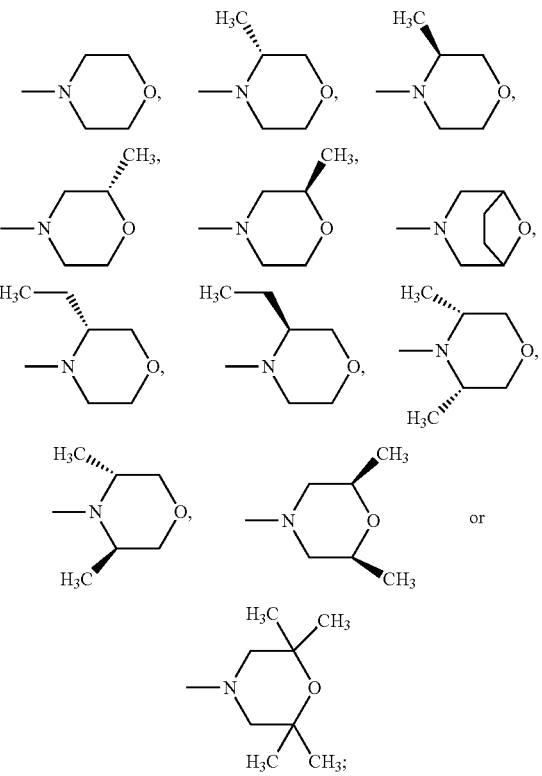

and preferably, $R^1$ is

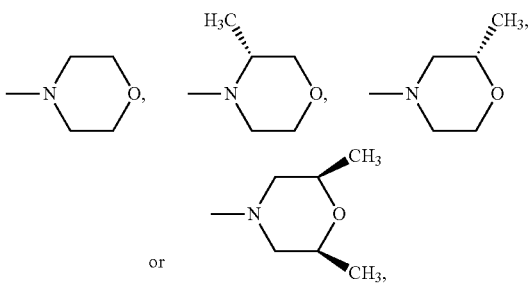

$R^2$ represents

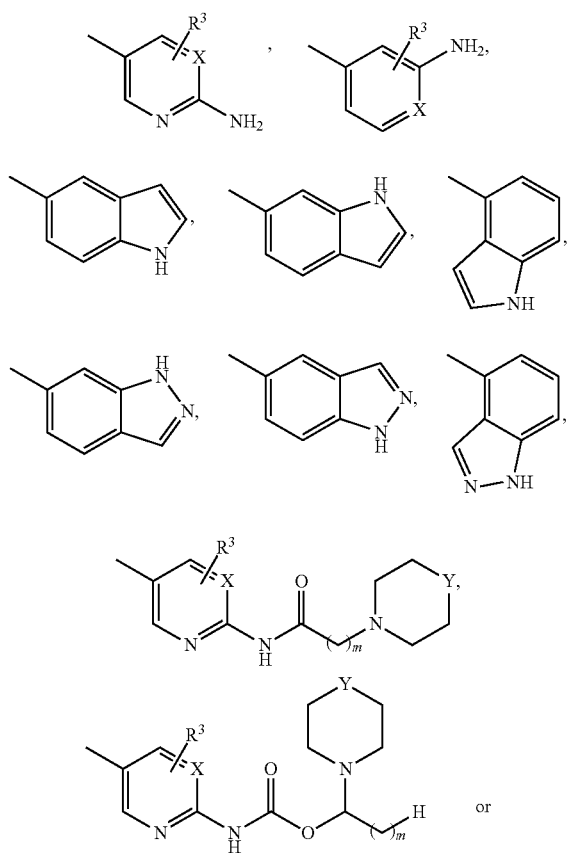

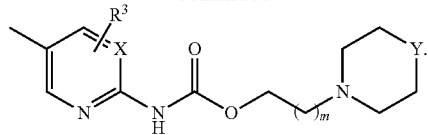

$R^3$ represents H, F, Br, Cl, $CF_3$, $CH_3$ or $OCH_3$. X represents CH or N. Y represents O, NH, $NCH_3$ or $CH_2$, and m=1 or 2. Preferably, $R^2$ is

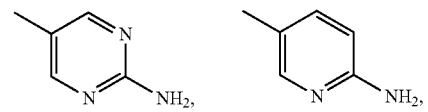

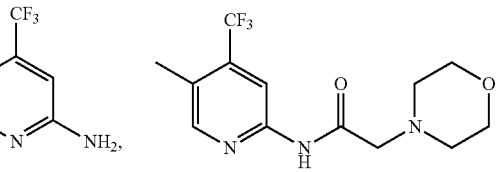

or

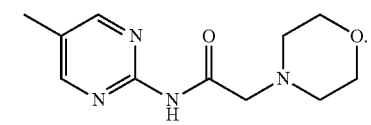

Some of more preferred compounds of the present disclosure are as follows:

| Code | Chemical name | Structural formula |
|---|---|---|
| I-1 | 4-(3-(2-(2-aminopyrimidin-5-yl)-4-morpholinyl-5,6,7,8-tetrahydropyrido[3,4-d]pyrimidin-7-formyl)-4-fluorobenzyl)phthalazin-1(2H)-one | |
| I-2 | 4-(3-(2-(6-aminopyridin-3-yl)-4-morpholinyl-5,6,7,8-tetrahydropyrido[3,4-d]pyrimidin-7-formyl)-4-fluorobenzyl)phthalazin-1(2H)-one | |

| Code | Chemical name | Structural formula |
|---|---|---|
| I-3 | 4-(3-(2-(6-amino-4-(trifluoromethyl)pyridin-3-yl)-4-morpholinyl-5,6,7,8-tetrahydropyrido[3,4-d]pyrimidin-7-formyl)-4-fluorobenzyl)phthalazin-1(2H)-one | |
| I-4 | N-(5-(7-(2-fluoro-5-((4-oxo-3,4-dihydrophthalazin-1-yl)methyl)benzoyl)-4-morpholinyl-5,6,7,8-tetrahydropyrido[3,4-c]pyrimidin-2-yl)-4-(trifluoromethyl)pyridin-2-yl)-2-morpholinyl acetamide | |
| I-5 | 4-(3-(2-(6-amino-5-(trifluoromethyl)pyridin-3-yl)-4-morpholinyl-5,6,7,8-tetrahydropyrido[3,4-d]pyrimidin-7-formyl)-4-fluorobenzyl)phthalazin-1(2H)-one | |
| I-6 | 4-(3-(2-(4-amino-2-fluorophenyl)-4-morpholinyl-5,6,7,8-tetrahydropyrido[3,4-d]pyrimidin-7-formyl)-4-fluorobenzyl)phthalazin-1(2H)-one | |
| I-7 | 4-(3-(2-(3-amino-4-fluorophenyl)-4-morpholinyl-5,6,7,8-tetrahydropyrido[3,4-d]pyrimidin-7-formyl)-4-fluorobenzyl)phthalazin-1(2H)-one | |

| Code | Chemical name | Structural formula |
|---|---|---|
| I-8 | 4-(3-(2-(1H-indazole-4-yl)-4-morpholinyl-5,6,7,8-tetrahydropyrido[3,4-d]pyrimidin-7-formyl)-4-fluorobenzyl)phthalazin-1(2H)-one | |
| I-9 | 4-(3-(2-(1H-indole-5-yl)-4-morpholinyl-5,6,7,8-tetrahydropyrido[3,4-d]pyrimidin-7-formyl)-4-fluorobenzyl)phthalazin-1(2H)-one | |
| I-10 | 4-(3-(2-(1H-indole-4-yl)-4-morpholinyl-5,6,7,8-tetrahydropyrido[3,4-d]pyrimidin-7-formyl)-4-fluorobenzyl)phthalazin-1(2H)-one | |
| I-11 | (S)-4-(3-(2-(2-aminopyrimidin-5-yl)-4-(3-methylmorpholinyl)-5,6,7,8-tetrahydropyrido[3,4-d]pyrimidin-7-formyl)-4-fluorobenzyl)phthalazin-1(2H)-one | |
| I-12 | 4-(3-(2-(2-aminopyrimidin-5-yl)-4-((2S,6R)-2,6-dimethylmorpholinyl)-5,6,7,8-tetrahydropyrido[3,4-d]pyrimidin-7-formyl)-4-fluorobenzyl)phthalazin-1(2H)-one | |

Some of the compounds of the formula (I) of the present disclosure can be prepared by the following method:

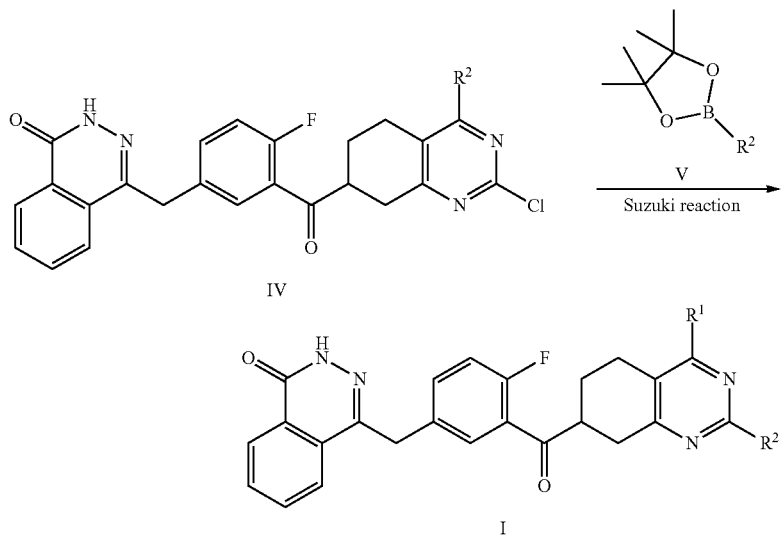

The above reaction is preferably performed under the conditions of adding a catalyst, a base and a reaction solvent, wherein the catalyst is preferably selected from palladium chloride, palladium acetate, bis(triphenylphosphine)palladium dichloride, tetrakis(triphenylphosphine)palladium, [1,1'-bis(diphenylphosphino)ferrocene]palladium dichloride or [1,1'-bis(diphenylphosphino)ferrocene]nickel dichloride; the base is preferably selected from sodium ethoxide, sodium acetate, potassium acetate, potassium phosphate, sodium carbonate or potassium carbonate; the reaction solvent is preferably selected from N,N-dimethylformamide, N,N-dimethylacetamide, ethylene glycol dimethyl ether, dioxane, tetrahydrofuran, toluene, ethanol, water or a mixed solvent of any two or three of the solvents; and a reaction temperature is preferably 80° C. to 120° C.

The catalyst is further preferably the tetrakis(triphenylphosphine)palladium; the base is further preferably the potassium carbonate; the solvent is further preferably a mixed solvent of the dioxane/water; and the reaction temperature is further preferably 100° C. to 110° C.

In more detail, if preparation is performed from starting raw materials (4) and (III), the method includes:

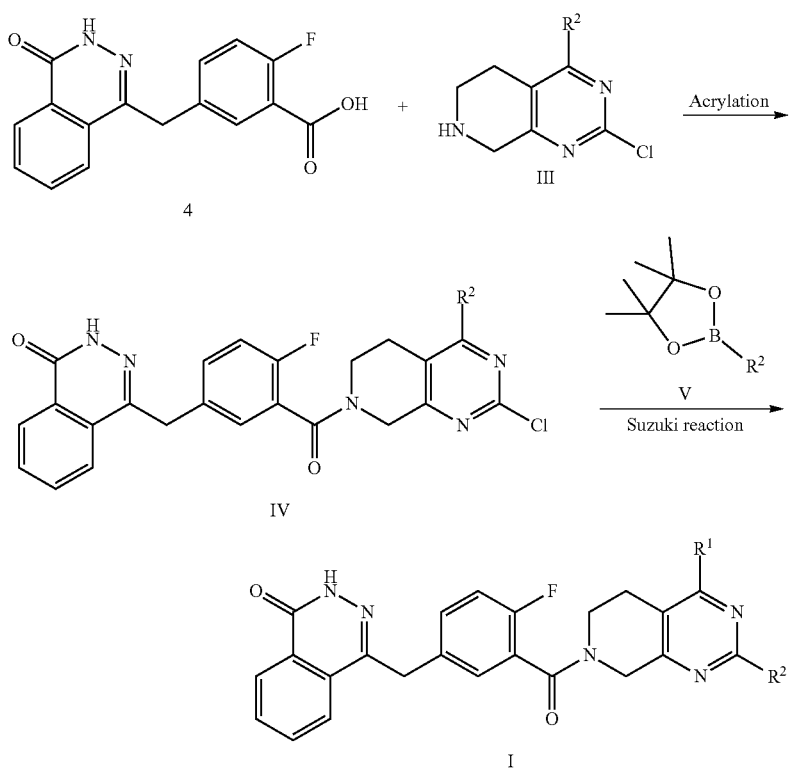

The process of preparing a compound IV from a compound 4 and a compound III via acylation:

A condensing agent used is preferably selected from benzotriazol-1-yl-oxytripyrrolidinylphosphonium hexafluorophosphate (PyBOP), 1-hydroxybenzotriazole (HOBt)/1-(3-dimethylaminopropyl)-3-ethylcarbodiimide hydrochloride (EDCI), dicyclohexylcarbodiimide (DCC) or N,N'-carbonyldiimidazole (CDI). More preferred is the PyBOP.

An acid binding agent is preferably selected from triethylamine, N,N-diisopropylethylamine (DIEA), 4-dimethylaminopyridine (DMAP), pyridine, sodium acetate, potassium acetate, sodium carbonate or potassium carbonate. More preferred is the DIEA.

The reaction solvent is preferably selected from N,N-dimethylformamide, N,N-dimethylacetamide or dimethyl sulfoxide. More preferred is the N,N-dimethylformamide.

The reaction temperature is preferably 10° C. to 80° C. More preferred is 20° C. to 40° C.

The process of preparing a compound I from the compound IV and borate V via Suzuki reaction:

The catalyst used is preferably selected from palladium chloride, palladium acetate, bis(triphenylphosphine)palladium dichloride, tetrakis(triphenylphosphine)palladium, [1,1'-bis(diphenylphosphino)ferrocene]palladium dichloride or [1,1'-bis(diphenylphosphino)ferrocene]nickel dichloride. More preferred is the tetrakis(triphenylphosphine)palladium.

The base is preferably selected from sodium ethoxide, sodium acetate, potassium acetate, potassium phosphate, sodium carbonate or potassium carbonate. More preferred is the potassium carbonate.

The reaction solvent is preferably selected from N,N-dimethylformamide, N,N-dimethylacetamide, ethylene glycol dimethyl ether, dioxane, tetrahydrofuran, toluene, ethanol, water or a mixed solvent of any two or three of the solvents. More preferred is a mixed solvent of the dioxane/water.

The reaction temperature is preferably 80° C. to 120° C. More preferred is 100° C. to 110° C.

In the process of preparing a compound I•A from the compound I via salt formation, a reactant A is hydrogen chloride, hydrogen bromide, sulfuric acid, phosphoric acid, carbonic acid, oxalic acid, citric acid, succinic acid, tartaric acid, lactic acid, pyruvic acid, acetic acid, maleic acid, methanesulfonic acid, benzenesulfonic acid, p-toluenesulfonic acid or ferulic acid; and a solvent is methanol, ethanol, dichloromethane, acetone, ethyl acetate, toluene, tetrahydrofuran or a mixed solvent of any two or three of the solvents.

The present disclosure further discloses a pharmaceutical composition, including a compound (I) with an effective drug dosage of the present disclosure or a salt and a pharmaceutically acceptable carrier thereof.

The pharmaceutically acceptable carrier can be added into the compounds of the present disclosure to prepare common pharmaceutical preparations, such as tablets, capsules, powders, syrups, liquids, suspensions, freeze-dried injections and injections, and common pharmaceutical excipients such as perfumes, sweetening agents, liquid or solid filler or diluents can be added.

The compounds of the present disclosure can be clinically administrated by oral administration, injection and other ways.

Generally, when the compounds of the present disclosure are used in therapy, a human dosage ranges from 1 mg to 1,000 mg per day. The dosage may also exceed the range according to different dosage forms and the severity of diseases.

Pharmacological experiments and results of some of the compounds of the present disclosure are as follows:

(1) Detection of inhibitory activity of the compounds on PARP-1 and PI3K at the enzyme level Experimental Method Test methods for kinase inhibitory activity used in this experiment are basically the same, except that different concentrations are adopted according to different kinases and different corresponding substrates to achieve the optimal detection range.

Experimental method for PARP-1 inhibitory activity: taking out a 96-well plate pre-coated with histones, and adding a following enzyme reaction system and inhibitors of different concentrations into each well, including: 50 μL of a reaction buffer solution (Tris*HCl, pH 8.0), $NAD^+$, biotin-labeled activated DNA, PARP-1 enzyme, and an inhibitor; after reaction at a room temperature for 1 hour, adding 50 uL of avidin-labeled HRP into each well for reaction for 30 minutes; and then adding 100 μL of an HRP substrate, and detecting a chemiluminescence value on a SpectraMax M instrument. The percentage of enzyme activity is calculated by the following formula:

Enzyme activity percentage (%)=(OD value administration hole−OD value background)/(OD value control hole−OD value background)×100%

Experimental method for PI3Kα inhibitory activity: simultaneously adding 40 mM Tris, pH 7.4, 10 mM $MgCl_2$, 0.1 mg/ml BSA, 1 mM DTT, 10 μM ATP, PI3Kα kinase and a kinase substrate into different concentrations of compounds to be sieved to form a 50 μL reaction system, after reaction at 30° C. for 40 minutes, detecting an ADP content in the system through a luciferase method, and then after reaction for 5 minutes, detecting a chemiluminescence signal on an MD-SpectraMax M5 multi-function microplate reader, wherein the intensity of a value of the chemiluminescence signal is in direct proportion to enzyme activity inhibition. The detected value of the chemiluminescence signal is substituted into the following formula:

Enzyme activity percentage (%)=(OD value administration hole−OD value background)/(OD value control hole−OD value background)×100%

The experiment results are shown in Table 1.

Method for determining $IC_{50}$ of PARP-1 and PI3Kα: diluting a drug concentration according to a three-fold concentration gradient, and detecting two duplicate wells at each concentration; taking the drug concentration as the abscissa and the percentage of enzyme activity corresponding to each concentration as the ordinate, and calculating to obtain inhibition $IC_{50}$ values of all tested compounds by using Graphpad Prism5 for nonlinear regression.

Some of the compounds with better enzyme inhibitory activity are selected for measuring their $IC_{50}$ values for PARP-1 and PI3Kα respectively. The experiment results are shown in Table 2.

TABLE 1

Inhibitory Activity of Tested Compounds on PARP-1 and PI3Kα under Measured Concentrations

| Number | Inhibition rate on PARP-1 (10 nM) | Inhibition rate on PI3Kα (100 nM) |
| --- | --- | --- |
| I-1 | 81% | 66% |
| I-2 | 93% | 66% |
| I-3 | 55% | 34% |
| I-4 | 67% | 53% |

TABLE 1-continued

Inhibitory Activity of Tested Compounds on
PARP-1 and PI3Kα under Measured Concentrations

| Number | Inhibition rate on PARP-1 (10 nM) | Inhibition rate on PI3Kα (100 nM) |
|---|---|---|
| I-5 | 81% | 17% |
| I-6 | 89% | 24% |
| I-7 | 83% | 27% |
| I-8 | 91% | 42% |
| I-9 | 85% | 30% |
| I-10 | 88% | 15% |
| I-11 | 94% | 67% |
| I-12 | 76% | 40% |

The results in Table 1 show that the compounds of the present disclosure have a high inhibitory activity against the PARP-1, and the tested compounds have the inhibition rate of more than 70% on the PARP-1 under a concentration of 10 nM; and the compounds also have a high inhibitory activity against the PI3Kα, and some of the compounds have the inhibition rate of more than 50% on the PI3Kα under a concentration of 100 nM. The above results show that the compounds of the present disclosure have double inhibitory activity against the PARP-1 and the PI3K.

TABLE 2

$IC_{50}$ Values of Some of Tested Compounds for PARP-I and PI3Kα

| | $IC_{50}$(nM) | |
|---|---|---|
| Number | PARP-1 | PI3Kα |
| I-1 | 3.75 | 69.0 |
| I-2 | 0.395 | 130.0 |
| I-3 | 4.90 | 194.2 |
| I-11 | 0.376 | 29.8 |
| I-12 | 3.87 | 92.6 |

The results in Table 2 show that the compounds of the present disclosure have a good inhibitory activity against the PARP-1 and the PI3K, and most of the compounds have better inhibitory activity against the PARP-1 than the PI3Kα, and a compound I-11 has the best activity, which has $IC_{50}$ of 0.376 nM for the PARP-1 and $IC_{50}$ of 29.8 nM for the PI3Kα.

(2) Detection of Inhibitory Activity of Compounds on Tumor Cell Proliferation

Experimental Method

Inoculating HCT116 (human colon cancer cells), HCC1937 (human breast cancer cells), MDA-MB-231 (human breast cancer cells) and MDA-MB-468 (human breast cancer cells) in a logarithmic growth phase with a certain quantity in a 96-well plate (200 μL/well) for culture for 24 hours so as to adhere to walls and then adding drugs. Arranging 3 duplicate wells for each drug concentration, and setting corresponding zero-cut holes and blank controls. After 72 hours of drug action, adding 50% TCA (50 μL/well) into adherent cells, fixing at 4° C. for 1 hour, pouring a fixing solution, washing for 5 times with distilled water, and naturally drying. Adding 100 μL of 4 mg/mL SRB into each well, staining at a room temperature for 15 minutes, discarding, washing for 5 times with 1% glacial acetic acid, and naturally drying. Finally, adding 150 μL of a 10 mM Tris solution into each well, shaking to be uniform, and measuring OD values at a wavelength of 565 nm using a wavelength-adjustable microplate reader (VERSAmax™, Molecular Device). A cell growth inhibition rate is calculated by the above formula, and the results are shown in Table 3.

TABLE 3

Test Results of In Vitro Antitumor Activity of Compounds

| | $IC_{50}$(μM) | | | |
|---|---|---|---|---|
| Number | HCT116 | HCC1937 | MDA-MB-231 | MDA-MB-468 |
| I-1 | 0.211 | 0.081 | 0.443 | 0.909 |
| I-2 | 0.217 | 0.121 | 0.816 | 1.344 |
| I-3 | 0.775 | 0.504 | 0.155 | 0.266 |
| I-8 | 0.536 | 0.482 | 0.708 | 1.152 |
| I-11 | 0.162 | 0.133 | 0.375 | 0.738 |
| I-12 | 1.012 | 0.784 | 1.127 | 1.583 |

The results in Table 3 show that the compounds of the present disclosure all have strong in vitro antitumor activity and can significantly inhibit the proliferation of tumor cells. The compounds not only have significant inhibitory activity against BRCA-deficient HCC1937 and HCT116 cells, but also have strong inhibitory activity against BRCA wild-type MDA-MB-231 and MDA-MB-468 cells. Among them, a compound I-1 has the strongest inhibitory activity against tumor cells HCC1937, and an $IC_{50}$ reaches 0.081 μM; and the $IC_{50}$ of compounds I-1, 1-3 and I-11 is less than 1.0 μM for the four tested tumor cells.

(3) Detection of Inhibitory Activity of Compounds on Growth of Human Breast Cancer MDA-MB-468 Cell Nude Mice Xenograft The test grouping condition is shown in Table 4.

TABLE 4

Test Grouping Condition and Drug Concentration Selection

| | Administration scheme | | | | |
|---|---|---|---|---|---|
| Group | Administration way | Administration dosage (mg/kg) | Solvent | Administration period | Administration frequency |
| Model group | Abdominal cavity | | DMSO | 34 days | Once every 2 days |
| Olaparib group | Abdominal cavity | 50 mg/kg | DMSO | 34 days | Once every 2 days |
| BKM120 group | Abdominal cavity | 27.5 mg/kg | DMSO | 34 days | Once every 2 days |
| Olaparib + BKM120 group | Abdominal cavity | 50 mg/kg + 27.5 mg/kg | DMSO | 34 days | Once every 2 days |
| 1-1 (low) | Abdominal cavity | 25 mg/kg | DMSO | 34 days | Once every 2 days |
| 1-1 (medium) | Abdominal cavity | 50 mg/kg | DMSO | 34 days | Once every 2 days |
| 1-1 (high) | Abdominal cavity | 100 mg/kg | DMSO | 34 days | Once every 2 days |
| 1-3 | Abdominal cavity | 50 mg/kg | DMSO | 34 days | Once every 2 days |

Experimental Method

Preparing an MDA-MB-468 cell line in a logarithmic growth phase into a $2\times10^7$/mL cell suspension under sterile conditions, and inoculating 0.1 mL of the cell suspension under the skin of the right axilla of each nude mouse. Measuring the diameter of a nude mice xenograft with a vernier caliper, and randomly dividing the animals into groups after the tumors grew to about 100 mm³. Dynamically observing an anti-tumor effect of the tested animals using a method of measuring the tumor diameter, wherein the frequency of measurements of the tumor diameter is once every 2 days, and the administration volume is 0.4 mL/20 g. After 34 days, killing the mice and surgically removing and weighing tumor pieces. The formula for calculating tumor volume (TV) is:

$TV = \frac{1}{2} \times a \times b^2$, wherein $a$ and $b$ represent the length and the width respectively.

The results are shown in Table 5 and Table 6.

TABLE 5

Influence of Compounds on Volumes of Human Breast Cancer MDA-MB-468 Cell Nude Mice Xenografts

| Compounds | Tumor Volumes (mm³) | | | | | | |
|---|---|---|---|---|---|---|---|
| | 0 day | 6 days | 12 days | 18 days | 24 days | 30 days | 34 days |
| Blank | 95.04 ± 4.08 | 185.72 ± 30.21 | 297.83 ± 30.04 | 455.65 ± 32.36 | 903.20 ± 53.00 | 1063.93 ± 60.48 | 1166.76 ± 68.10 |
| Olaparib | 96.41 ± 4.82 | 222.00 ± 27.97 | 324.20 ± 38.65 | 422.84 ± 38.55 | 566.86 ± 29.26 | 718.76 ± 27.46 | 834.87 ± 70.65 |
| BKM120 | 94.67 ± 4.20 | 203.83 ± 17.57 | 294.34 ± 28.54 | 388.09 ± 36.86 | 525.13 ± 53.13 | 677.51 ± 51.92 | 777.59 ± 54.84 |
| Olaparib + BKM120 | 96.66 ± 4.05 | 156.62 ± 13.58 | 253.45 ± 12.62 | 329.39 ± 22.10 | 433.72 ± 37.57 | 537.51 ± 55.28 | 602.56 ± 67.84 |
| I-1 (low) | 96.16 ± 4.43 | 205.61 ± 11.10 | 303.37 ± 20.74 | 401.23 ± 26.08 | 555.25 ± 26.17 | 707.38 ± 28.67 | 808.40 ± 24.64 |
| I-1 (medium) | 94.95 ± 4.84 | 136.45 ± 11.01 | 222.15 ± 27.78 | 301.78 ± 38.32 | 399.10 ± 47.33 | 489.89 ± 43.78 | 551.70 ± 40.89 |
| I-1 (high) | 93.30 ± 4.20 | 122.80 ± 3.00 | 145.60 ± 5.70 | 186.00 ± 7.00 | 209.30 ± 7.30 | 234.10 ± 9.40 | 250.00 ± 9.30 |
| I-3 | 93.00 ± 4.70 | 142.00 ± 7.90 | 190.90 ± 6.30 | 216.60 ± 5.10 | 241.50 ± 6.70 | 280.80 ± 5.70 | 310.10 ± 7.50 |

TABLE 6

Influence of Compounds on Tumor Weights of Human Breast Cancer MDA-MB-468 Cell Nude Mice Xenografts

| Compounds | Blank | Olaparib | BKM120 | Olaparib + BKM120 | I-1 (low) | I-1 (medium) | I-1 (high) | I-3 |
|---|---|---|---|---|---|---|---|---|
| Tumor weights | 2.05 ± 0.43 | 1.55 ± 0.34 | 1.36 ± 0.26 | 0.76 ± 0.15 | 0.85 ± 0.17 | 0.54 ± 0.13 | 0.34 ± 0.06 | 0.44 ± 0.10 |

It can be known from Tables 5 and 6 that the compounds I-1 (50 mg/kg), 1-3 (50 mg/kg) and olaparib (50 mg/kg)/BKM120 (27.5 mg/kg) of the present disclosure can be combined to significantly inhibit the growth of the MDA-MB-468 nude mice xenografts, and the inhibition rate is higher than that of positive drugs olaparib and BKM120; and the anti-tumor effects of the compound I-1 (50 mg/kg) and 1-3 (50 mg/kg) are obviously superior to that of the combination group ($p<0.05$) of olaparib (50 mg/kg)/BKM120 (27.5 mg/kg), and the anti-tumor effect of the compound 1-3 is the optimal. Meanwhile, the compound I-1 can inhibit tumor growth in a dose-dependent manner.

DETAILED DESCRIPTION OF THE INVENTION

Embodiment 1

Synthesis of 4-(3-(2-(2-aminopyrimidin-5-yl)-4-morpholinyl-5,6,7,8-tetrahydropyrido[3,4-d]pyrimidin-7-formyl)-4-fluorobenzyl)phthalazin-1(2H)-one (I-1)

7-benzyl-5,6,7,8-tetrahydropyrido[3,4-d]pyrimidin-2,4(1H,3H)-dione (2)

Ethyl 1-benzyl-3-oxopiperidine-4-carboxylate hydrochloride (1) (40.0 g, 134.33 mmol) and urea (17.09 g, 282.01 mmol) were added into a 500 mL three-necked flask, 250 mL of absolute methanol was added and stirred to be dissolved, the temperature was reduced to 0° C., and a methanol solution of sodium methoxide (228.0 mL, 1.0 mol/L) was dropwise added. After dropwise addition, heating reflux reaction under nitrogen protection was performed for about 20 hours. TLC (petroleum ether: ethyl acetate=5:1) was adopted to detect that the raw material 1 was completely reacted, heating was stopped, a mixture was cooled to the room temperature, a large amount of white solids were precipitated, and the temperature was reduced to 0° C. Stirring was continued for 1 hour, suction filtration was carried out, and a filter cake was washed with 50 mL of methanol to obtain a white solid. The white solid was dissolved in 400 mL of water and adjusted to be neutral with 1 mol/L hydrochloric acid, and a large amount of solids were precipitated. Suction filtration and drying were carried out to obtain 27.68 g of a white solid with the yield of 80.1%. Without purification, the white solid was directly applied to the next step.

7-benzyl-2,4-dichloro-5,6,7,8-tetrahydropyrido[3,4-d]pyrimidine (3)

200 mL of phosphorus oxychloride was added to a 500 mL three-necked flask, and the temperature was reduced to 0° C. A compound 2 (27.68 g, 107.58 mmol) was slowly added. After the addition, a reaction solution was pink and cloudy. Under nitrogen protection, heating reflux reaction was performed for 6-8 hours. TLC (petroleum ether: ethyl acetate=3:1) was adopted to detect that the raw material 2 was completely reacted, heating was stopped, a mixture was slightly cooled, and the phosphorus oxychloride was evaporated under reduced pressure. A residue was slowly poured into 400 g of crushed ice, the pH was adjusted to 8 to 9 with a 5 mol/L NaOH solution, and a solid was precipitated. Suction filtration was carried out, and a filter cake was washed with water and dried to obtain 29.0 g of an off-white solid with the yield of 91.6%. $^1$HNMR (300 MHz, CDCl$_3$) δ (ppm): 7.34-7.29 (5H, m, ArH), 3.75 (2H, s, CH$_2$), 3.67 (2H, s, CH$_2$), 2.85 (4H, m, 2×CH$_2$).

4-(7-benzyl-2-chloro-5,6,7,8-tetrahydropyrido[3,4-d]pyrimidin-4-yl)morpholine (II-1)

The compound 3 (29.0 g, 98.58 mmol) was dissolved in a mixed solvent of isopropanol (200 mL) and dichloromethane (20 mL), and morpholine (10.31 g, 118.30 mmol) and DIEA (32.59 mL, 197.16 mmol) were slowly added. After the addition, the temperature was raised to 50° C. for reaction for 3 to 5 hours, TLC (petroleum ether: ethyl acetate=9:1) was adopted to detect that the raw material 3 was completely reacted, heating was stopped, the temperature was reduced to the room temperature, a solid was precipitated, and the temperature was reduced to 0° C. Stirring was continued for 30 minutes, suction filtration was carried out, and a filter cake was washed with 50 mL of isopropanol and dried to obtain 23.0 g of an off-white solid. A filtrate was concentrated under reduced pressure, a residue was dissolved with 200 mL of ethyl acetate and washed with water (100 mL) and a saturated sodium chloride solution (100 mL) in sequence, and concentration under reduced pressure was performed to obtain a yellow grease. Column chromatography purification (petroleum ether: ethyl acetate=50:1 to 5:1) was performed to obtain 7.42 g of a white solid, and 30.42 g of a product was obtained in total with the yield of 89.5%. m.p. 154-156° C. $^1$HNMR (300 MHz, DMSO-d$_6$) δ (ppm): 7.34-7.23 (5H, m, ArH), 3.66-3.62 (6H, m, 2×CH$_2$), 3.47-3.44 (6H, m, 3×CH$_2$), 2.65-2.54 (4H, m, 2×CH$_2$).

4-(2-chloro-5,6,7,8-tetrahydropyrido[3,4-d]pyrimidin-4-yl)morpholine (III-1)

A compound 4 (21.10 g, 61.19 mmol) was dissolved in 200 mL of dichloromethane and cooled to 0° C. in an ice bath, 1-chloroethyl chloroformate (26.41 mL, 244.76 mmol) was added dropwise, and after the addition, a mixture was stirred with heat preservation for 30 minutes. The temperature was raised to 25° C., and stirring was performed for reaction for 8 to 10 hours. TLC (petroleum ether: ethyl acetate=1:1) was adopted to detect that the raw material 4 was completely reacted, and the solvent was evaporated under reduced pressure. 200 mL of methanol was added for reflux reaction for 1 hour, and the solvent was evaporated under reduced pressure. 200 mL of water was added to dissolve a residue, and the pH was adjusted to 8 to 9 with a 1 mol/L NaOH solution. Dichloromethane (150 mL×3) was adopted for extraction, an organic layer was combined, a saturated sodium chloride solution (200 mL×2) was adopted for washing, and drying was performed with anhydrous Na$_2$SO$_4$. Suction filtration was carried out, a filtrate was concentrated, and a residue was subjected to column chromatography purification (dichloromethane:methanol=80:1 to 20:1 for gradient elution) to obtain 10.5 g of a yellow solid with the yield of 67.4%. $^1$HNMR (300 MHz, DMSO-d$_6$) δ (ppm): 3.75-3.64 (6H, m, 3×CH$_2$), 3.44-3.41 (4H, m, 2×CH$_2$), 2.79 (2H, m, CH$_2$), 2.66 (1H, s, NH), 2.50-2.48 (2H, m, CH$_2$).

4-(3-(2-chloro-4-morpholinyl-5,6,7,8-tetrahydropyrido[3,4-d]pyrimidin-7-formyl)-4-fluorobenzyl)phthalazin-1(2H)-one (IV-1)

2-fluoro-5-((4-oxo-3,4-dihydrophthalazin)methyl)benzoic acid (4) (11.24 g, 37.68 mmol), 4-(2-chloro-5,6,7,8-tetrahydropyrido[3,4-d]pyrimidin-4-yl)morpholine (III-1) (9.60 g, 37.69 mmol) and PyBOP (23.54 g, 45.23 mmol) were added into a 200 mL three-necked flask. 100 mL of DMF was added and stirred to be dissolved, and then DIEA (24.92 mL, 150.79 mmol) was added and stirred at 25° C. for reaction for 6-8 hours. TLC (dichloromethane:methanol=20:1) was adopted to detect that the raw material 4 was completely reacted, a reaction solution was poured into 300 mL of water, and a large amount of solids were precipitated. Suction filtration was carried out, a filter cake was washed with 100 mL of water and dried to obtain a crude product, and column chromatography purification (dichloromethane:methanol=100:1 to 20:1 for gradient elution) was performed to obtain 12.06 g of an off-white solid with the yield of 59.8%. m.p. 174-177° C. $^1$HNMR (300 MHz, DMSO-d$_6$) δ (ppm): 12.61 (1H, s, CONH), 8.29-8.25 (1H, m, ArH), 7.98 (1H, d, J=7.7 Hz, ArH), 7.92-7.80 (2H, m, ArH), 7.52-7.40 (2H, m, ArH), 7.32-7.24 (1H, m, ArH), 4.63 (1H, s, 0.5×CH$_2$), 4.36 (2H, s, CH$_2$), 4.29 (1H, s, 0.5×CH$_2$), 3.85-3.61 (5H, m, 2.5×CH$_2$), 3.54-3.42 (4H, m, 2×CH$_2$), 3.29-3.13 (1H, m, 0.5×CH$_2$), 2.74-2.57 (2H, m, CH$_2$).

4-(3-(2-(2-aminopyrimidin-5-yl)-4-morpholinyl-5,6,7,8-tetrahydropyrido[3,4-d]pyrimidin-7-formyl)-4-fluorobenzyl)phthalazin-1(2H)-one (I-1)

The compound IV-1 (9.06 g, 16.94 mmol) and 5-(4,4,5,5-tetramethyl-1,3,2-dioxaborolan-2-yl)pyrimidin-2-amine (V-1) (5.61 g, 25.40 mmol) were added into a 250 mL reaction flask, and 100 mL of dioxane was added and stirred to be dissolved. K$_2$CO$_3$ (9.37 g, 67.76 mmol) was dissolved in 10 mL of water, a reaction solution was added slowly, and then tetratriphenylphosphine palladium (0.98 g, 0.85 mmol) was added. Under nitrogen protection, heating reflux reaction was performed for 4 to 6 hours to precipitate a yellow solid. TLC (dichloromethane:methanol=20:1) was adopted to detect that the raw material IV-1 was completely reacted, and a mixture was cooled to the room temperature. Suction filtration was performed, and a filter cake was washed with water (40 mL) and ethyl acetate (20 mL) in sequence and dried to obtain a crude product. 120 mL of ethyl acetate was added and beaten for 2 hours, and suction filtration and drying were carried out to obtain 5.80 g of a light-yellow solid with the yield of 57.7%. m.p. 159-160° C. $^1$HNMR (300 MHz, DMSO-d$_6$) δ (ppm): 12.73 (1H, s, CONH), 9.16

(1H, s, ArH), 9.07 (1H, s, ArH), 8.37 (1H, t, J=6.8 Hz, ArH), 8.11-7.88 (3H, m, ArH), 7.63-7.54 (2H, m, ArH), 7.40 (1H, t, J=8.7 Hz, ArH), 7.30 (2H, s, $NH_2$), 4.81 (1H, s, 0.5×$CH_2$), 4.47 (2H, s, $CH_2$), 4.45 (1H, s, 0.5×$CH_2$), 3.95-3.55 (10H, m, 5×$CH_2$), 2.85-2.71 (2H, m, $CH_2$). $^{13}$CNMR (75 MHz, DMSO-$d_6$) δ (ppm): 164.12, 163.67, 162.66, 160.27, 159.89, 159.34, 157.75, 154.92, 144.85, 134.85, 133.44, 132.01, 131.54, 129.05, 127.85, 126.03, 125.43, 123.67, 119.47, 117.77, 115.88, 112.42, 65.97, 50.45, 47.69, 46.43, 36.44, 26.14. HRMS (ESI): m/z [M+H]$^+$. Calcd for $C_{31}H_{28}FN_9O_3$: 594.2372; Found: 594.2371.

Embodiment 2

Synthesis of 4-(3-(2-(6-aminopyrimidin-3-yl)-4-morpholinyl-5,6,7,8-tetrahydropyrido[3,4-d]pyrimidin-7-formyl)-4-fluorobenzyl)phthalazin-1(2H)-one (I-2)

A compound IV-1 (300 mg, 0.56 mmol) and 5-(4,4,5,5-tetramethyl-1,3,2-dioxaborolan-2-yl)pyridin-2-amine (V-2) (136 mg, 0.62 mmol) were added into a 100 mL three-necked flask, and 20 mL of dioxane was added and stirred to be dissolved. $K_2CO_3$ (310 mg, 2.24 mmol) was dissolved in 2 mL of water, a reaction solution was added, and then tetratriphenylphosphine palladium (65 mg, 0.06 mmol) was added. Under nitrogen protection, heating reflux reaction was performed for 4 to 5 hours. TLC (dichloromethane:methanol=20:1) was adopted to detect that the raw material IV-1 was completely reacted, heating was stopped, and a mixture was cooled to the room temperature. Suction filtration was performed, a filtrate was concentrated, a residue was added into 40 mL of ethyl acetate, a mixed solution was washed with water (20 mL×1) and a saturated sodium chloride solution (20 mL×2) in sequence, and drying was performed with anhydrous $Na_2SO_4$. Suction filtration was performed, a filtrate was concentrated, and a residue was subjected to column chromatography purification (dichloromethane:methanol=100:1 to 30:1) to obtain 220 mg of a light-yellow solid with the yield of 66.3%. m.p. 206-207° C. $^1$HNMR (300 MHz, DMSO-$d_6$) δ (ppm): 12.61 (1H, s, CONH), 8.89-8.80 (1H, m, ArH), 8.28-8.12 (2H, m, ArH), 8.00-7.78 (3H, m, ArH), 7.51-7.45 (2H, m, ArH), 7.29 (1H, t, J=9.1 Hz, ArH), 6.51-6.47 (1H, m, ArH), 6.44 (2H, s, $NH_2$), 4.69 (1H, s, 0.5×$CH_2$), 4.36 (2H, s, $CH_2$), 4.33 (1H, s, 0.5×$CH_2$), 3.88-3.47 (10H, m, 5×$CH_2$), 2.73-2.58 (2H, m, $CH_2$). $^{13}$CNMR (75 MHz, DMSO-$d_6$) δ (ppm): 164.39, 163.78, 161.00, 160.22, 159.84, 159.37, 154.97, 148.57, 144.84, 136.17, 134.88, 133.43, 132.04, 131.52, 129.07, 127.88, 126.04, 125.42, 123.77, 121.29, 116.10, 115.83, 111.90, 107.18, 65.98, 47.77, 46.51, 43.74, 36.47, 26.03. HRMS (ESI): m/z [M+H]$^+$. Calcd for $C_{32}H_{29}FN_8O_3$: 593.2419; Found: 593.2418.

Embodiment 3

Synthesis of 4-(3-(2-(6-amino-4-(trifluoromethyl) pyridin-3-yl)-4-morpholinyl-5,6,7,8-tetrahydropyrido[3,4-d]pyrimidin-7-formyl)-4-fluorobenzyl) phthalazin-1(2H)-one (1-3)

With the compound IV-1 (1.0 g, 1.87 mmol) and 5-(4,4,5,5-tetramethyl-1,3,2-dioxaborolan-2-yl)-4-(trifluoromethyl)pyridin-2-amine (V-3) (646 mg, 2.24 mmol) as raw materials, operation was the same as the method of I-2, and column chromatography purification (dichloromethane:methanol=100:1 to 20:1 for gradient elution) was carried out to obtain 680 mg of a light-yellow solid with the yield of 55.1%. m.p. 158-160° C. $^1$HNMR (300 MHz, DMSO-$d_6$) δ (ppm): 12.56 (1H, s, CONH), 8.51-8.42 (1H, m, ArH), 8.25 (1H, t, J=7.3 Hz, ArH), 7.98-7.75 (3H, m, ArH), 7.50-7.43 (2H, m, ArH), 7.30-7.22 (1H, m, ArH), 6.82 (1H, s, ArH), 6.80 (2H, s, $NH_2$), 4.68 (1H, s, ½Ar$CH_2$N), 4.35 (2H, s, Ar$CH_2$), 4.32 (1H, s, ½Ar$CH_2$N), 3.84-3.39 (10H, m, 5$CH_2$), 2.76-2.60 (2H, m, N$CH_2CH_2$). $^{13}$CNMR (75 MHz, DMSO-$d_6$) δ (ppm): 164.43, 164.03, 163.55, 160.50, 159.82, 159.37, 158.22, 154.98, 152.35, 144.79, 135.56, 134.89, 133.38, 131.96, 131.47, 129.08, 127.90, 126.03, 125.38, 123.47, 121.34, 119.67, 116.10, 112.56, 104.37, 66.00, 47.70, 46.29, 43.64, 36.50, 25.99. HRMS (ESI): m/z [M+H]$^+$. Calcd for $C_{33}H_{28}F_4N_8O_3$: 661.2293; Found: 661.2298.

Embodiment 4

Synthesis of 4-(3-(2-(6-amino-5-(trifluoromethyl) pyridin-3-yl)-4-morpholinyl-5,6,7,8-tetrahydropyrido[3,4-d]pyrimidin-7-formyl)-4-fluorobenzyl) phthalazin-1(2H)-one (I-5)

With the compound IV-1 (300 mg, 0.56 mmol) and 5-(4,4,5,5-tetramethyl-1,3,2-dioxaborolan-2-yl)-3-(trifluoromethyl)pyridin-2-amine (V-4) (178 mg, 0.62 mmol) as raw materials, operation was the same as the method of 1-2, and column chromatography purification (dichloromethane:methanol=100:1 to 40:1) was carried out to obtain 250 mg of a light-yellow solid with the yield of 67.6%. m.p. 256-258° C. $^1$HNMR (300 MHz, DMSO-$d_6$) δ (ppm): 12.61 (1H, s, CONH), 9.11-9.03 (1H, m, ArH), 8.51-8.41 (1H, m, ArH), 8.26 (1H, t, J=7.2 Hz, ArH), 8.00-7.76 (3H, m, ArH), 7.56-7.44 (2H, m, ArH), 7.29 (1H, t, J=8.7 Hz, ArH), 7.01 (2H, s, $NH_2$), 4.71 (2H, s, $CH_2$), 4.36 (2H, s, $CH_2$), 3.93-3.39 (10H, m, 5×$CH_2$), 2.75-2.61 (2H, m, $CH_2$). $^{13}$CNMR (75 MHz, DMSO-$d_6$) δ (ppm): 164.40, 163.93, 160.42, 160.06, 159.35, 157.93, 156.51, 152.23, 144.81, 137.91, 134.97, 133.87, 133.41, 131.94, 131.50, 129.61, 129.09, 128.84, 127.90, 126.04, 125.43, 123.71, 120.89, 116.11, 112.64, 65.96, 47.72, 46.48, 43.71, 36.47, 26.12. HRMS (ESI): m/z [M+H]$^+$. Calcd for $C_{33}H_{28}F_4N_8O_3$: 661.2293; Found: 661.2290.

Embodiment 5

Synthesis of 4-(3-(2-(4-amino-2-fluorophenyl)-4-morpholinyl-5,6,7,8-tetrahydropyrido[3,4-d]pyrimidin-7-formyl)-4-fluorobenzyl)phthalazin-1(2H)-one (I-6)

With the compound IV-1 (300 mg, 0.56 mmol) and 3-fluoro-4-(4,4,5,5-tetramethyl-1,3,2-dioxaborolan-2-yl) aniline (V-5) (147 mg, 0.62 mmol) as raw materials, operation was the same as the method of I-2, and column chromatography purification (dichloromethane:methanol=100:1 to 50:1 for gradient elution) was carried out to obtain 145 mg of a light-yellow solid with the yield of 42.5%. m.p. 204-206° C. $^1$HNMR (300 MHz, DMSO-$d_6$) δ (ppm): 12.58 (1H, s, CONH), 8.28-8.22 (1H, s, ArH), 8.00-7.68 (4H, m, ArH), 7.51-7.43 (2H, m, ArH), 7.30-7.25 (1H, m, ArH), 6.44-6.27 (2H, m, ArH), 5.81 (2H, s, $NH_2$), 4.65 (1H, s, 0.5×$CH_2$), 4.35 (2H, s, $CH_2$), 4.30 (1H, s, 0.5×$CH_2$), 3.82-3.38 (10H, m, 5×$CH_2$), 2.72-2.57 (2H, m, $CH_2$). $^{13}$CNMR (75 MHz, DMSO-$d_6$) δ (ppm): 164.37, 163.99, 163.53, 160.07, 159.36, 152.55, 144.84, 134.88, 133.43, 132.10, 131.53, 129.06, 128.79, 127.87, 126.04, 125.43, 123.77, 123.50, 121.31, 115.85, 112.61, 111.47, 109.46, 100.48, 100.09, 65.96, 47.76, 46.44, 43.70, 36.46, 25.96. HRMS (ESI): m/z [M+H]$^+$. Calcd for $C_{33}H_{29}F_2N_7O_3$: 610.2373; Found: 610.2368.

Embodiment 6

Synthesis of 4-(3-(2-(3-amino-4-fluorophenyl)-4-morpholinyl-5,6,7,8-tetrahydropyrido[3,4-d]pyrimidin-7-formyl)-4-fluorobenzyl)phthalazin-1(2H)-one (I-7)

With the compound IV-1 (300 mg, 0.56 mmol) and 2-fluoro-5-(4,4,5,5-tetramethyl-1,3,2-dioxaborolan-2-yl) aniline (V-6) (147 mg, 0.62 mmol) as raw materials, operation was the same as the method of I-2, and column chromatography purification (dichloromethane:methanol=100:1 to 50:1 for gradient elution) was carried out to obtain 160 mg of a light-yellow solid with the yield of 46.9%. m.p. 236-239° C. $^1$HNMR (300 MHz, DMSO-d$_6$) δ (ppm): 12.59 (1H, s, CONH), 8.25 (1H, t, J=6.6 Hz, ArH), 7.97 (1H, d, J=7.8 Hz, ArH), 7.91-7.71 (3H, m, ArH), 7.58-7.42 (3H, m, ArH), 7.29 (1H, t, J=9.0 Hz, ArH), 7.15-7.04 (1H, m, ArH), 4.74 (1H, s, 0.5×CH$_2$), 4.38 (1H, s, 0.5×CH$_2$), 4.35 (2H, m, CH$_2$), 3.84-3.39 (10H, m, 5×CH$_2$), 2.77-2.62 (2H, m, CH$_2$). $^{13}$CNMR (75 MHz, DMSO-d$_6$) δ (ppm): 164.43, 164.02, 163.28, 159.36, 158.34, 154.99, 144.80, 138.50, 134.89, 133.42, 132.18, 131.52, 129.09, 128.81, 127.90, 126.04, 125.42, 123.55, 117.40, 116.62, 116.15, 115.87, 115.18, 114.93, 112.34, 66.01, 47.81, 45.59, 43.55, 36.48, 26.21. HRMS (ESI): m/z [M+H]$^+$. Calcd for $C_{33}H_{29}F_2N_7O_3$: 610.2373; Found: 610.2374.

Embodiment 7

Synthesis of 4-(3-(2-(1H-indazole-4-yl)-4-morpholinyl-5,6,7,8-tetrahydropyrido[3,4-d]pyrimidin-7-formyl)-4-fluorobenzyl)phthalazin-1(2H)-one (I-8)

With the compound IV-1 (300 mg, 0.56 mmol) and 4-(4,4,5,5-tetramethyl-1,3,2-dioxaborolan-2-yl)-1H-indazole (V-7) (151 mg, 0.62 mmol) as raw materials, operation was the same as the method of I-2, and column chromatography purification (dichloromethane:methanol=100:1 to 40:1) was carried out to obtain 130 mg of a light-yellow solid with the yield of 37.6%. m.p. 198-200° C. $^1$HNMR (300 MHz, DMSO-d$_6$) δ (ppm): 13.24 (1H, s, NH), 12.60 (1H, s, CONH), 8.82-8.70 (1H, m, ArH), 8.28-8.07 (2H, m, ArH), 7.97 (t, J=7.2 Hz, 1H), 7.91-7.72 (2H, m, ArH), 7.67 (1H, t, J=7.0 Hz, ArH), 7.50-7.40 (3H, m, ArH), 7.32-7.25 (1H, m, ArH), 4.83 (1H, s, 0.5×CH$_2$), 4.46 (1H, s, 0.5×CH$_2$), 4.36 (2H, s, CH$_2$), 3.88-3.49 (10H, m, 5×CH$_2$), 2.80-2.66 (2H, m, CH$_2$). $^{13}$CNMR (75 MHz, DMSO-d$_6$) δ (ppm): 169.67, 164.47, 164.19, 160.48, 159.36, 158.23, 154.85, 144.82, 140.74, 134.99, 133.42, 131.93, 131.52, 130.29, 129.10, 127.91, 126.05, 125.42, 123.76, 123.51, 121.14, 120.79, 116.12, 115.83, 113.43, 112.42, 66.03, 48.04, 46.56, 43.68, 36.49, 26.18. HRMS (ESI): m/z [M+H]$^+$. Calcd for $C_{34}H_{29}FN_8O_3$: 617.2419; Found: 617.2425.

Embodiment 8

Synthesis of 4-(3-(2-(1H-indole-5-yl)-4-morpholinyl-5,6,7,8-tetrahydropyrido[3,4-d]pyrimidin-7-formyl)-4-fluorobenzyl)phthalazin-1(2H)-one (I-9)

With the compound IV-1 (300 mg, 0.56 mmol) and 5-(4,4,5,5-tetramethyl-1,3,2-dioxaborolan-2-yl)-1H-indole (V-8) (151 mg, 0.62 mmol) as raw materials, operation was the same as the method of I-2, and column chromatography purification (dichloromethane:methanol=100:1 to 60:1 for gradient elution) was carried out to obtain 153 mg of a light-yellow solid with the yield of 44.4%. m.p. 238-240° C. $^1$HNMR (300 MHz, DMSO-d$_6$) δ (ppm): 12.59 (1H, s, CONH), 11.24 (1H, s, NH), 8.60-8.51 (1H, m, ArH), 8.26 (1H, t, J=6.5 Hz, ArH), 8.18-8.05 (1H, m, ArH), 8.00-7.75 (3H, m, ArH), 7.50-7.36 (4H, m, ArH), 7.28 (1H, t, J=8.9 Hz, ArH), 6.53 (1H, d, J=9.6 Hz, ArH), 4.73 (1H, s, 0.5×CH$_2$), 4.38 (1H, s, 0.5×CH$_2$), 4.36 (2H, s, CH$_2$), 3.86-3.40 (10H, m, 5×CH$_2$), 2.75-2.61 (2H, m, CH$_2$). $^{13}$CNMR (75 MHz, DMSO-d$_6$) (ppm): 164.41, 164.05, 161.34, 160.29, 159.92, 159.36, 151.00, 144.83, 137.37, 134.99, 133.43, 131.90, 131.52, 129.09, 128.49, 127.90, 127.59, 126.05, 125.44, 121.11, 120.19, 117.44, 116.13, 112.10, 111.01, 102.17, 90.23, 66.02, 47.87, 46.56, 43.76, 36.50, 26.05. HRMS (ESI): m/z [M+H]$^+$. Calcd for $C_{35}H_{30}FN_7O_3$: 616.2467; Found: 616.2462.

Embodiment 9

Synthesis of 4-(3-(2-(1H-indole-4-yl)-4-morpholinyl-5,6,7,8-tetrahydropyrido[3,4-d]pyrimidin-7-formyl)-4-fluorobenzyl)phthalazin-1(2H)-one (I-10)

With the compound IV-1 (300 mg, 0.56 mmol) and 4-(4,4,5,5-tetramethyl-1,3,2-dioxaborolan-2-yl)-1H-indole (V-9) (151 mg, 0.62 mmol) as raw materials, operation was the same as the method of 1-2, and column chromatography purification (dichloromethane:methanol=100:1 to 60:1 for gradient elution) was carried out to obtain 125 mg of an off-white solid with the yield of 36.3%. m.p. 178-181° C. $^1$HNMR (300 MHz, DMSO-d$_6$) δ (ppm): 12.62 (1H, s, CONH), 11.29 (1H, s, NH), 8.26 (1H, t, J=8.9 Hz, ArH), 8.12 (1H, d, J=6.9 Hz, ArH), 8.02-7.74 (4H, m, ArH), 7.55-7.40 (4H, m, ArH), 7.34-7.14 (2H, m, ArH), 4.80 (1H, s, 0.5×CH$_2$), 4.45 (1H, s, 0.5×CH$_2$), 4.37 (2H, s, CH$_2$), 3.90-3.46 (10H, m, 5×CH$_2$), 2.80-2.66 (2H, m, CH$_2$). $^{13}$CNMR (75 MHz, DMSO-d$_6$) δ (ppm): 164.47, 164.10, 162.16, 160.20, 159.89, 159.35, 158.23, 151.45, 144.82, 140.70, 137.03, 134.91, 133.42, 132.03, 131.51, 129.10, 128.85, 127.89, 126.10, 125.41, 123.79, 120.36, 116.11, 115.85, 113.69, 112.56, 103.32, 66.05, 48.09, 46.59, 43.77, 36.49, 26.05. HRMS (ESI): m/z [M+H]$^+$. Calcd for $C_{35}H_{30}FN_7O_3$: 616.2467; Found: 616.2464.

Embodiment 10

Synthesis of (S)-4-(3-(2-(2-aminopyrimidin-5-yl)-4-(3-methylmorpholinyl)-5,6,7,8-tetrahydropyrido[3,4-d]pyrimidin-7-formyl)-4-fluorobenzyl)phthalazin-1(2H)-one (I-11)

(S)-4-(7-benzyl-2-chloro-5,6,7,8-tetrahydropyrido[3,4-d]pyrimidin-4-yl)-3-methylmorpholine (II-2)

An intermediate 3 (2.0 g, 6.80 mmol) was dissolved in a mixed solvent of isopropanol (20 mL) and dichloromethane (4 mL), and (S)-3-methylmorpholine (0.83 g, 8.20 mmol) and DIEA (2.24 mL, 13.56 mmol) were slowly added. After the addition, the temperature was raised to 50° C. for reaction for 8 to 10 hours. TLC (petroleum ether: ethyl acetate=9:1) was adopted to detect that a raw material 3 was completely reacted, heating was stopped, and a mixture was slightly cooled. The solvent was evaporated under reduced pressure, a residue was dissolved by 50 mL of ethyl acetate and washed with water (50 mL) and a saturated sodium chloride solution (50 mL×2) in sequence, and drying was performed with anhydrous $Na_2SO_4$. Suction filtration was carried out, a filtrate was concentrated under reduced pressure to obtain a yellow grease, and column chromatography purification (petroleum ether: ethyl acetate=20:1 to 5:1 for gradient elution) was performed to obtain 1.4 g of a yellow solid with the yield of 57.4%. $^1$HNMR (300 MHz, $CDCl_3$) δ (ppm): 7.39-7.30 (5H, m, ArH), 4.18-4.11 (1H, m, 0.5× $CH_2$), 3.97-3.92 (1H, m, 0.5×$CH_2$), 3.78-3.44 (9H, m, 4×$CH_2$, CH), 2.82-2.57 (4H, m, 2×$CH_2$), 1.34 (3H, d, J=6.8 Hz, $CH_3$).

(S)-4-(2-chloro-5,6,7,8-tetrahydropyrido[3,4-d]pyrimidin-4-yl)-3-methylmorpholine (III-2)

An intermediate 11-2 (1.10 g, 3.07 mmol) was dissolved in 20 mL of dichloromethane, and the temperature was reduced to 0° C. 1-chloroethyl chloroformate (1.43 mL, 13.28 mmol) was added dropwise and stirred with heat preservation for 15 min. The temperature was raised to 25° C., and stirring was performed for reaction for 6 to 10 hours. TLC (petroleum ether: ethyl acetate=1:1) was adopted to detect that the raw material II-2 was completely reacted, and a solvent was evaporated under reduced pressure. 20 mL of methanol was added for reflux reaction for 30 minutes. A solvent was evaporated under reduced pressure, a residue was dissolved in 20 mL of water, the pH was adjusted to 8 to 9 with a 1 mol/L NaOH solution, dichloromethane (30 mL×3) was adopted for extraction, an organic layer was combined, a saturated sodium chloride solution (40 mL×3) was adopted for washing, and drying was performed with anhydrous $Na_2SO_4$. Suction filtration was carried out, a filtrate was concentrated to obtain a brown grease, and column chromatography purification (dichloromethane:methanol=40:1 to 5:1 for gradient elution) was carried out to obtain 550 mg of a yellow solid with the yield of 66.7%. $^1$HNMR (300 MHz, $CDCl_3$) δ (ppm): 4.12 (1H, m, 0.5× $CH_2$), 3.99 (2H, s, $CH_2$), 3.95-3.91 (1H, m, 0.5×$CH_2$), 3.78-3.59 (4H, m, 2×$CH_2$), 3.53-3.43 (1H, m, CH), 3.14-3.07 (1H, m, 0.5×$CH_2$), 3.00-2.92 (1H, m, 0.5×$CH_2$), 2.66-2.53 (2H, m, $CH_2$), 2.29 (1H, s, NH), 1.32 (3H, d, J=6.8 Hz, $CH_3$).

(S)-4-(3-(2-chloro-4-(3-methylmorpholinyl)-5,6,7,8-tetrahydropyrido[3,4-d]pyrimidin-7-formyl)-4-fluorobenzyl)phthalazin-1(2H)-one (IV-2)

A compound 4 (555 mg, 1.86 mmol), a compound 111-2 (500 mg, 1.86 mmol) and PyBOP (1.16 g, 2.23 mmol) were added into a 100 mL three-necked flask, 20 mL of DMF was added and stirred to be dissolved, and then DIEA (1.08 mL, 6.51 mmol) was added and stirred at 25° C. for reaction for 6-8 hours. TLC (dichloromethane:methanol=20:1) was adopted to detect that the raw material 111-2 was completely reacted, a reaction solution was poured into 60 mL of water, and a yellow solid was precipitated. Suction filtration was carried out, and a filter cake was washed with 20 mL of water and dried to obtain a crude product. Column chromatography purification (dichloromethane:methanol=100:1 to 20:1 for gradient elution) was carried out to obtain 740 mg of a yellow solid with the yield of 72.5%. m.p. 144-147° C. $^1$HNMR (300 MHz, $CDCl_3$) δ (ppm): 10.82 (1H, s, CONH), 8.51-8.46 (1H, m, ArH), 7.83-7.70 (3H, m, ArH), 7.45-7.36 (2H, m, ArH), 7.12-7.04 (1H, m, ArH), 4.46 (1H, s, 0.5× $CH_2$), 4.33 (1H, s, 0.5×$CH_2$), 4.30 (2H, s, $CH_2$), 4.17-4.06 (2H, m, $CH_2$), 3.95 (2H, m, $CH_2$), 3.73-3.51 (7H, m, 3×$CH_2$, CH), 1.38 (3H, d, J=6.7 Hz, $CH_3$).

(S)-4-(3-(2-(2-aminopyrimidin-5-yl)-4-(3-methylmorpholinyl)-5,6,7,8-tetrahydropyrido[3,4-d]pyrimidin-7-formyl)-4-fluorobenzyl)phthalazin-1(2H)-one (I-11)

With the compound IV-2 (300 mg, 0.55 mmol) and the compound V-1 (181 mg, 0.82 mmol) as raw materials, operation was the same as the method of 1-2, and column chromatography purification (dichloromethane:methanol=60:1 to 20:1 for gradient elution) was carried out to obtain 170 mg of a light-yellow solid with the yield of 50.9%. m.p. 214-216° C. $^1$HNMR (300 MHz, DMSO-$d_6$) δ (ppm): 12.60 (1H, s, CONH), 9.03 (1H, s, ArH), 8.94 (1H, s, ArH), 8.25 (1H, t, J=6.7 Hz, ArH), 7.99-7.76 (3H, m, ArH), 7.49-7.42 (2H, s, ArH), 7.28 (1H, t, J=9.1 Hz, ArH), 7.15 (2H, s, $NH_2$), 4.78-4.58 (H, m, 0.5×$CH_2$), 4.35 (2H, s, $CH_2$), 4.16-4.04 (H, m, 0.5×$CH_2$), 3.87-3.38 (9H, m, 4×$CH_2$, CH), 2.71-2.58 (2H, m, $CH_2$), 1.23 (3H, d, J=7.2 Hz, $CH_3$). $^{13}$CNMR (75 MHz, DMSO-$d_6$) δ (ppm): 164.36, 164.13, 163.63, 160.35, 159.97, 159.35, 157.67, 144.83, 134.88, 133.43, 132.01, 131.53, 129.04, 127.87, 126.82, 126.03, 125.44, 123.71, 123.45, 119.53, 116.10, 112.56, 70.27, 66.25, 49.54, 46.52, 43.71, 42.06, 36.45, 26.15, 14.09. HRMS (ESI): m/z $[M+H]^+$. Calcd for $C_{32}H_{30}FN_9O_3$: 608.2528; Found: 608.2535.

Embodiment 11

Synthesis of 4-(3-(2-(2-aminopyrimidin-5-yl)-4-((2S,6R)-2,6-dimethylmorpholinyl)-5,6,7,8-tetrahydropyrido[3,4-d]pyrimidin-7-formyl)-4-fluorobenzyl)phthalazin-1(2H)-one (I-12)

(2S,6R)-4-(7-benzyl-2-chloro-5,6,7,8-tetrahydropyrido[3,4-d]pyrimidin-4-yl)-2,6-dimethylmorpholine (II-3)

A compound 3 (2.0 g, 6.80 mmol) was dissolved in 30 mL of isopropanol, 4 mL of dichloromethane was added to assist dissolution, and (2R,6S)-2,6-dimethylmorpholine (0.94 g, 8.16 mmol) and DIEA (2.24 mL, 13.56 mmol) were slowly added. After the addition, the temperature was raised to 50° C. for reaction for 8 to 10 hours. TLC (petroleum ether: ethyl acetate=9:1) was adopted to detect that the raw material 3 was completely reacted, and a mixture was slightly cooled. A solvent was evaporated under reduced pressure, a residue was dissolved in 100 mL of ethyl acetate and washed with water (50 mL) and a saturated sodium chloride solution (50 mL×2) in sequence, and drying was performed with anhydrous $Na_2SO_4$. Suction filtration was carried out, a filtrate was concentrated to obtain 1.86 g of a yellow grease with the yield of 73.2%, and the yellow grease was directly used in the next step of reaction without purification.

(2S,6R)-4-(2-chloro-5,6,7,8-tetrahydropyrido[3,4-d]pyrimidin-4-yl)-2,6-dimethylmorpholine (III-3)

The compound 11-3 (1.66 g, 4.45 mmol) was dissolved in 20 mL of dichloromethane, and the temperature was reduced to 0° C. 1-chloroethyl chloroformate (2.08 mL, 19.24 mmol) was added dropwise and stirred with heat preservation for 15 minutes. The temperature was raised to 25° C., and stirring was carried out for reaction for 8 to 10 hours. TLC (petroleum ether: ethyl acetate=1:1) was adopted to detect that the raw material II-3 was completely reacted, and a solvent was evaporated under reduced pressure. 20 mL of methanol was added, and heating reflux reaction was performed for 30 minutes. A solvent was evaporated under reduced pressure, a residue was dissolved in 20 mL of water, and the pH was adjusted to 8 to 9 with a 1 mol/L NaOH solution. Dichloromethane (20 mL×3) was adopted for extraction, an organic layer was combined, washing was performed with a saturated sodium chloride solution (30 mL×2), and drying was performed with anhydrous $Na_2SO_4$. Suction filtration was carried out, a filtrate was concentrated to obtain a brown grease, and column chromatography purification (dichloromethane:methanol=40:1 to 5:1 for gradient elution) was carried out to obtain 0.90 g of a yellow solid with the yield of 71.4%.

4-(3-(2-chloro-44(2S,6R)-2,6-dimethylmorpholinyl)-5,6,7,8-tetrahydropyrido[3,4-d]pyrimidine-7-formyl)-4-fluorobenzyl)phthalazin-1(2H)-one (IV-3)

An intermediate 4 (0.95 g, 3.19 mmol), the compound III-3 (0.90 g, 3.18 mmol) and PyBOP (1.99 g, 3.82 mmol) were added into a 50 mL three-necked flask, and 20 mL of DMF was added and stirred to be dissolved. Then DIEA (1.84 mL, 11.14 mmol) was added and stirred at 25° C. for reaction for 6 to 8 hours. TLC (dichloromethane:methanol=20:1) was adopted to detect that the raw material 111-3 was completely reacted, and a reaction solution was poured into 60 mL of water to precipitate a yellow solid. Suction filtration was carried out, and a filter cake was washed with 20 mL of water and dried to obtain a crude product. Column chromatography purification (dichloromethane:methanol=100:1 to 40:1 for gradient elution) was carried out to obtain 1.02 g of a yellow solid with the yield of 57.0%. m.p. 149-152° C. $^1$HNMR (300 MHz, CDCl$_3$) δ (ppm): 11.03 (1H, s, CONH), 8.51-8.46 (1H, m, ArH), 7.83-7.70 (3H, m, ArH), 7.46-7.35 (2H, m, ArH), 7.12-7.04 (1H, m, ArH), 4.45 (1H, s, 0.5×CH$_2$), 4.33 (1H, s, 0.5×CH$_2$), 4.30 (2H, s, CH$_2$), 3.92-3.67 (6H, m, 2×CH$_2$, 2×CH), 2.78-2.74 (4H, m, 2×CH$_2$), 1.27-1.23 (6H, m, 2CH$_3$).

4-(3-(2-(2-aminopyrimidin-5-yl)-4-((2S,6R)-2,6-dimethylmorpholinyl)-5,6,7,8-tetrahydropyrido[3,4-d]pyrimidin-7-formyl)-4-fluorobenzyl)phthalazin-1(2H)-one (I-12)

With the compound IV-3 (300 mg, 0.53 mmol) and the compound V-1 (177 mg, 0.80 mmol) as raw materials, operation was the same as the method of 1-2, and column chromatography purification (dichloromethane:methanol=100:1 to 20:1 for gradient elution) was carried out to obtain 160 mg of a light-yellow solid with the yield of 48.6%. m.p. 204-206° C. $^1$HNMR (300 MHz, DMSO-d$_6$) δ (ppm): 12.60 (1H, s, CONH), 9.03 (1H, s, ArH), 8.94 (1H, s, ArH), 8.25 (1H, t, J=6.9 Hz, ArH), 8.00-7.76 (3H, m, ArH), 7.50-7.42 (2H, m, ArH), 7.27 (1H, t, J=9.0 Hz, ArH), 7.14 (2H, s, NH$_2$), 4.68 (1H, s, 0.5×CH$_2$), 4.35-4.32 (3H, m, 1.5×CH$_2$), 3.95-3.79 (3H, m, 1.5×CH$_2$), 3.69-3.62 (2H, m, 2CH), 3.42-3.38 (1H, m, 0.5×CH$_2$), 2.74-2.58 (4H, m, 2×CH$_2$), 1.14 (3H, d, J=6.2 Hz, CH$_3$), 1.09 (3H, d, J=6.1 Hz, CH$_3$). $^{13}$CNMR (75 MHz, DMSO-d$_6$) δ (ppm): 164.42, 164.13, 163.38, 160.31, 159.88, 159.34, 157.74, 154.81, 144.81, 134.74, 133.41, 132.07, 131.50, 129.10, 127.89, 126.07, 125.43, 123.53, 119.45, 116.21, 115.82, 112.38, 70.95, 52.63, 46.49, 43.75, 36.47, 26.15, 18.59. HRMS (ESI): m/z [M+H]$^+$. Calcd for $C_{33}H_{32}FN_9O_3$: 622.2685; Found: 622.2691.

What is claimed is:

1. A compound of a formula I or a pharmaceutically acceptable salt thereof:

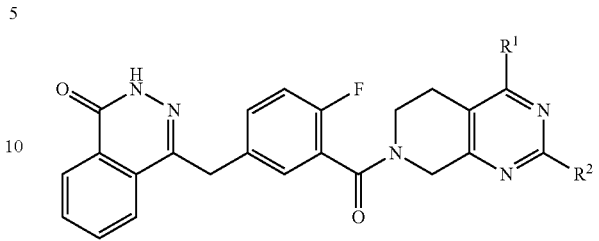

wherein $R^1$ represents

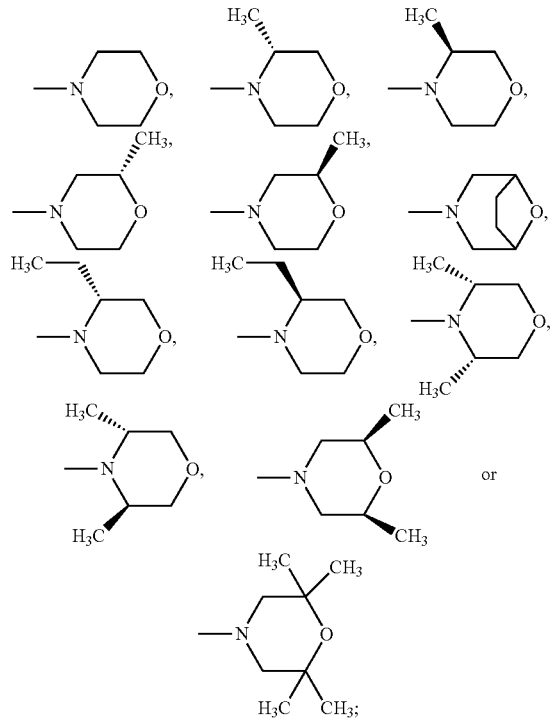

$R^2$ represents

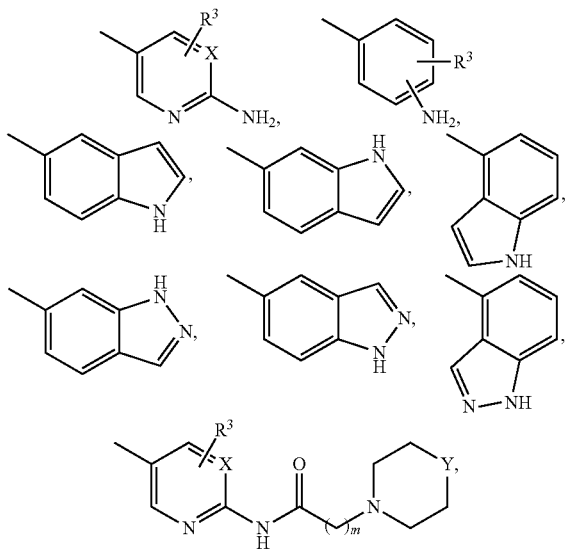

-continued

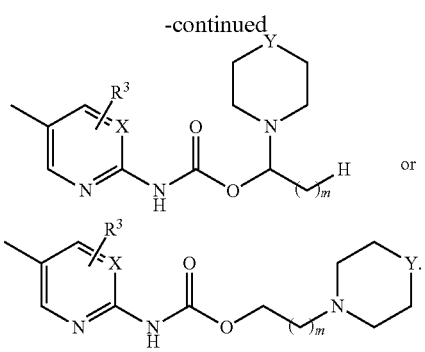

and R³ represents H, F, Br, Cl, CF₃, CN, CH₃ or OCH₃; X represents CH or N; Y represents O, NH, NCH₃ or CH₂; and m=1 or 2.

2. The compound or the pharmaceutically acceptable salt thereof according to claim 1, wherein R¹ represents

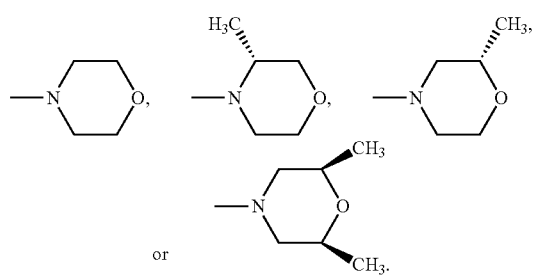

3. The compound or the pharmaceutically acceptable salt thereof according to claim 1, wherein R² represents

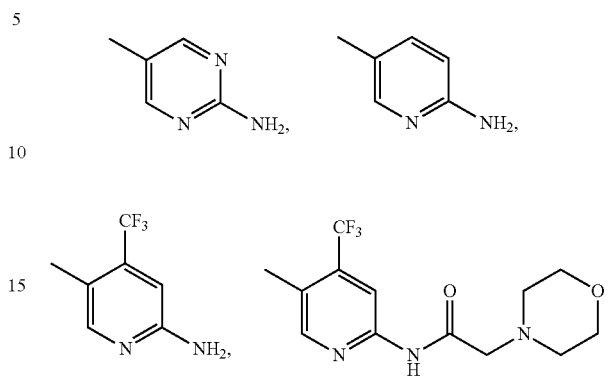

or

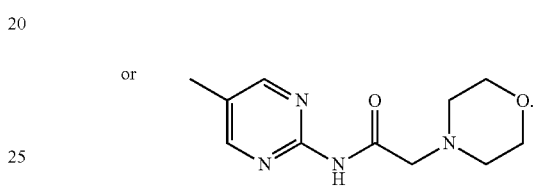

4. The compound or the pharmaceutically acceptable salt thereof according to claim 1, wherein the compound is prepared by the following reaction:

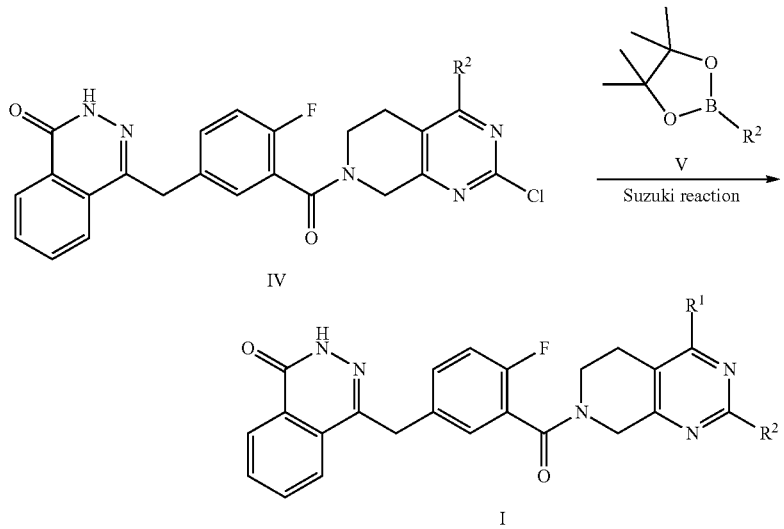

wherein R¹ and R² are as defined in claim 1.

5. The compound or the pharmaceutically acceptable salt thereof according to claim 4, wherein the Suzuki reaction is performed under the conditions of adding a catalyst, a base and a reaction solvent, and the catalyst is selected from bis(triphenylphosphine)palladium dichloride, tetrakis(triphenylphosphine)palladium or [1,1'-bis(diphenylphosphino) ferrocene]palladium dichloride; the base is selected from sodium ethoxide, sodium acetate, potassium acetate, potassium phosphate, sodium carbonate or potassium carbonate; the reaction solvent is selected from N,N-dimethylformamide, N,N-dimethylacetamide, ethylene glycol dimethyl ether, dioxane, tetrahydrofuran, toluene, ethanol, water or a mixed solvent of any two or three of the solvents; and a reaction temperature is 80° C. to 120° C.

6. The compound or the pharmaceutically acceptable salt thereof according to claim 5, wherein the catalyst is the tetrakis(triphenylphosphine)palladium; the base is the potassium carbonate; the solvent is a mixed solvent of the dioxane and the water; and the reaction temperature is 100° C. to 110° C.

7. The compound or the pharmaceutically acceptable salt thereof according to claim 1, wherein the pharmaceutically acceptable salt is an acid addition salt of the compound of the formula (I), wherein an acid used for forming the salt is: hydrogen chloride, hydrogen bromide, sulfuric acid, carbonic acid, oxalic acid, citric acid, succinic acid, tartaric acid, phosphoric acid, lactic acid, pyruvic acid, acetic acid, maleic acid, methanesulfonic acid, benzenesulfonic acid, p-toluenesulfonic acid or ferulic acid.

8. A pharmaceutical composition, comprising the compound or the pharmaceutically acceptable salt thereof according to claim 1 and a pharmaceutically acceptable carrier.

9. A pharmaceutical drug comprising a therapeutically effective amount of the compound or the pharmaceutically acceptable salt thereof according to claim 1 for treating a tumor, wherein the pharmaceutical drug is capable of inhibiting activities of PARP-1 and PI3K in the tumor.

10. The pharmaceutical drug according to claim 9, wherein the pharmaceutical drug is used for treating a subject with the tumor that expresses the activities of the PARP-1 or/and PI3K.

11. A method for treating a cancer comprising a step of administrating a therapeutically effective amount of the compound or the pharmaceutically acceptable salt thereof of claim 1 to a subject in need, wherein cell of the cancer over-expresses the PARP-1 or/and PI3K.

12. The method according to claim 11, wherein the cancer is selected from the group consisting of a colon cancer, a breast cancer and an ovarian cancer.

* * * * *

UNITED STATES PATENT AND TRADEMARK OFFICE
CERTIFICATE OF CORRECTION

PATENT NO. : 11,572,359 B2
APPLICATION NO. : 16/769893
DATED : February 7, 2023
INVENTOR(S) : Yungen Xu et al.

It is certified that error appears in the above-identified patent and that said Letters Patent is hereby corrected as shown below:

On the Title Page

Assignee should be:
(73) Assignee: CHINA PHARMACEUTICAL UNIVERSITY Nanjing (CN); HEFEI INDUSTRIAL PHARMACEUTICAL INSTITUTE CO., LTD., Hefei (CN)

Signed and Sealed this
Twenty-first Day of March, 2023

Katherine Kelly Vidal
*Director of the United States Patent and Trademark Office*